United States Patent

Lewis et al.

Patent Number: 5,770,041
Date of Patent: Jun. 23, 1998

[54] NON-ENOLIZABLE OXYGENATES AS ANTIFOULANTS

[75] Inventors: Vincent E. Lewis, Missouri City; Robert D. McClain; Michael K. Poindexter, both of Sugar Land, all of Tex.

[73] Assignee: Nalco/Exxon Energy Chemicals, L.P., Sugar Land, Tex.

[21] Appl. No.: 804,050

[22] Filed: Feb. 21, 1997

[51] Int. Cl.$^6$ .................................................. C10G 9/16
[52] U.S. Cl. ................................. 208/48 AA; 208/48 R; 208/295; 585/950
[58] Field of Search ............................ 208/48 AA, 48 R, 208/295; 585/950

[56] References Cited

U.S. PATENT DOCUMENTS

| | | | |
|---|---|---|---|
| 3,024,277 | 3/1962 | Hotten | 208/48 AA |
| 3,173,770 | 3/1965 | Thompson et al. | 208/48 AA |
| 3,364,130 | 1/1968 | Barnum et al. | 208/48 AA |
| 4,673,489 | 6/1987 | Roling | 208/289 |
| 4,952,301 | 8/1990 | Awbrey | 208/48 AA |
| 5,160,425 | 11/1992 | Lewis | 208/95 |
| 5,194,143 | 3/1993 | Roling | 208/291 |
| 5,220,104 | 6/1993 | McDaniel | 585/853 |
| 5,264,114 | 11/1993 | Dunbar | 208/48 AA |
| 5,288,394 | 2/1994 | Lewis et al. | 208/48 AA |
| 5,527,447 | 6/1996 | Roof | 208/48 AA |
| 5,614,080 | 3/1997 | Roof | 208/48 AA |

*Primary Examiner*—Walter D. Griffin
*Attorney, Agent, or Firm*—Elaine M. Ramesh; Thomas M. Breininger

[57] ABSTRACT

The invention is a method of inhibiting the formation of fouling deposits occurring on the surface of an alkaline scrubber used to remove acid gases, such as hydrogen sulfide, carbon dioxide and mercaptans, from hydrocarbon streams. These deposits are formed during the scrubbing of pyrolytically produced hydrocarbons contaminated with oxygen-containing compounds with a caustic solution having a pH>7 which comprises adding an effective deposit-inhibiting amount of a non-enolizable carbonyl compound to the caustic solution. The invention is also a method of inhibiting the formation of fouling deposits occurring in spent caustic wash/stripper systems used for hydrocarbon manufacturing processes. Fouling occurs in these systems when they are in contact with hydrocarbon processing streams contaminated with oxygen-containing compounds, such as aldehydes. These deposits are formed in hydrocarbon processing streams contaminated with oxygen-containing compounds while in contact with a caustic solution having a pH>7. The invention comprises adding an effective deposit-inhibiting amount of a non-enolizable carbonyl compound to the caustic solution. Preferred non-enolizable carbonyl compounds are formaldehyde, glyoxal, benzaldehyde, p-anisaldehyde, formic acid, glyoxalic acid and paraformaldehyde.

16 Claims, No Drawings

NON-ENOLIZABLE OXYGENATES AS ANTIFOULANTS

FIELD OF THE INVENTION

The invention is a method of inhibiting the formation of fouling deposits occurring on the surface of an alkaline scrubber used to remove acid gases, such as hydrogen sulfide, carbon dioxide and mercaptans, from hydrocarbon streams. These deposits are formed during the scrubbing of pyrolytically produced hydrocarbons contaminated with oxygen-containing compounds with a caustic solution having a pH>7 which comprises adding an effective deposit-inhibiting amount of a non-enolizable carbonyl compound to the caustic solution. The invention is also a method of inhibiting the formation of fouling deposits occurring in spent caustic wash/stripper systems used for hydrocarbon manufacturing processes. Fouling occurs in these systems when they are in contact with hydrocarbon processing streams contaminated with oxygen-containing compounds, such as aldehydes. These deposits are formed in hydrocarbon processing streams contaminated with oxygen-containing compounds while in contact with a caustic solution having a pH>7. The invention comprises adding an effective deposit-inhibiting amount of a non-enolizable carbonyl compound to the caustic solution. Preferred non-enolizable carbonyl compounds are formaldehyde, glyoxal, benzaldehyde, p-anisaldehyde, formic acid, glyoxalic acid and paraformaldehyde.

BACKGROUND OF THE INVENTION

A major problem encountered in the treatment of various hydrocarbon charge stocks is the phenomenon recognized as and descriptively called fouling. This phenomenon is manifested in the form of deposits which frequently form on the metal surfaces of the processing equipment and tend to decrease the efficiency of the intermediate processing operations. The results of fouling appear in the form of heat transfer loss, increased pressure drop and a loss in throughput rate. Fouling also increases the safety risks associated with operating a chemical process. It is therefore a beneficial practice to inhibit the build-up of deposits in processing equipment that would otherwise reduce capacity and overall plant efficiency.

In non-catalytic cracking operations, hydrocarbon streams undergo pyrolytic cracking to form unsaturated hydrocarbons. Typical streams used in cracking operations include ethane, propane, naphtha, kerosene, gas oil, fuel oil, mixtures thereof and the like. During pyrolytic cracking, oxygenated hydrocarbons, including carbonyl compounds such as acetaldehyde, are also formed. The concentration of carbonyl hydrocarbons, such as aldehydes and ketones, formed in such operations can vary widely. Carbonyl compounds, particularly aldehydes are known to be a source of polymeric foulants, when in contact with caustic. These polymeric foulants are known to lead to equipment fouling and to be a source of contaminants that can adversely affect product stream purity. Many of these oxygenated hydrocarbons are formed during the cracking operation. However, oxygenated hydrocarbons can also be introduced or formed through other means including intentional or inadvertent introduction of gases containing oxygen, such as air, or water containing dissolved air or oxygen, into process streams.

Typically, a cracker effluent stream must be rapidly cooled to stop or quench pyrolysis. Depending on the type of feedstock being cracked, the quenching of the cracker effluent can include either a one stage or a two stage quenching process. When light feedstocks, e.g., ethane, propane or the like, are cracked, the effluent is generally subjected to a one stage quench, while the effluent from the cracking of heavy feedstocks, e.g., naphtha, and the like, is generally subjected to a two stage quench.

In the case of the two stage quench, the effluent is first quenched in a primary fractionation unit, also sometimes called an oil quench unit, which cools (quenches) the cracker effluent to stop the pyrolytic reaction by injecting an oil or liquid hydrocarbon that is quickly evaporated. Typically, the liquid hydrocarbon is pyrolysis gasoline. This oil quench results in a primary, rough fractionation of the effluent into a light hydrocarbon fraction or distillate and a heavy hydrocarbon fraction. In a typical hydrocarbon cracking facility, such as an ethylene manufacturing plant which is cracking heavy feedstocks, the distillate of the primary fractionator includes light hydrocarbons and pyrolysis gasoline, while the heavy hydrocarbon fraction includes pyrolysis fuel oil.

The distillate product from the primary fractionator or the cracker effluent derived from the cracking of light feedstocks is then cooled with water to further quench the pyrolytic reaction in a water quench unit. The water quench unit also results in a fractionation of the cracker effluent stream. The lighter, more volatile hydrocarbons are taken overhead for subsequent processing, while the bottoms are withdrawn to a settling tank to separate water from the heavier, less volatile hydrocarbons. The aqueous phase is then recycled to the water quench unit.

In the case of the two stage quench, the heavier hydrocarbons taken from the bottoms of the water quench unit are refluxed to the top of the primary fractionator while in the case of a one stage quench the heavier hydrocarbons may be subjected to the downstream processing. Typically, in a two stage quench, the heavier hydrocarbons from the water quench unit are predominantly pyrolysis gasoline.

The quench units were designed to operate in the absence of basic materials such as caustic or the like. Therefore, fouling due to the presence of carbonyl compounds is not a significant problem.

After quenching and primary fractionating, the cracked effluent stream is introduced into a compression unit which subjects the stream to a series of compressors to increase the density of the stream and reduce its volume.

The quenched and compressed effluent hydrocarbon stream is then typically washed free of acidic contaminants in an aqueous basic wash unit. The basic wash unit can include amine acid gas scrubbers (e.g., monoethanolamine, diethanolamine, isopropyl amine, butyl amine, etc.) and/or caustic wash systems. In some ethylene production facilities, an amine scrubber is used in front of the caustic tower to remove most of the acid gases. In other facilities, only a caustic scrubber is used, and in still other facilities only an amine unit is present.

During the basic wash (pH>7), oxygenated hydrocarbons, such as carbonyl compounds, are partially removed along with the acidic components, such as hydrogen sulfide, carbon dioxide and mercaptans. Unfortunately, the removal conditions in the basic wash tower lead to base (pH>7) induced condensation reactions of the carbonyl compounds, especially aldehydes (e.g., acetaldehyde) and/or ketones. These condensation reactions eventually result in the formation of polymers. The resulting polymers can settle on internal surfaces of the unit, such as trays, packing, heat exchangers, reboilers and caustic circulation lines among others which leads to fouling and eventual equipment plugging. Ultimately, the unit must be shut down for cleaning—a costly operation.

In present-day cracker operations, it is desirable and environmentally preferable that any entrained hydrocarbons or residual organics be removed prior to disposal or further use of spent basic wash streams. Ordinarily, this is accomplished by washing the spent basic wash streams with pyrolysis gasoline in a liquid-liquid extraction vessel or other similar equipment, often referred to as a spent caustic wash system. The aqueous and hydrocarbon phases are then allowed to separate, over a period of time, in a settling tank before the two phases are withdrawn.

In the case of a two stage quench operation, the hydrocarbon phase withdrawn from the settling tank, essentially pyrolysis gasoline, is refluxed to the primary fractionator. The cleaned spent caustic stream can be drawn off and treated through neutralization, steam stripping, wet air oxidation biological treatment, or combinations of such treatments.

Although oxygenated hydrocarbons are found in many, if not all, operational units downstream from the cracker unit, these contaminants generally do not cause fouling problems alone. However, the carbonyl compounds formed in the cracker unit or elsewhere in a hydrocarbon cracking facility are known to cause fouling in caustic wash systems or scrubbers where the quenched and compressed effluent hydrocarbon stream is washed free of any hydrogen sulfide, carbon dioxide, mercaptans or other acidic contaminants. Additionally the conditions in a spent caustic wash/stripper are prone to condensation reactions of the carbonyl compounds, especially many enolizable aldehydes and/or ketones.

The amount of carbonyl compounds, such as aldehydes and ketones, formed in such operations can vary widely, but is typically about 1–100 ppm in the gas stream with concentrations as high as 1000 ppm occasionally being encountered because of the utilization of various feedstocks and cracking temperatures. When the gas stream is passed through a basic wash (pH>7) to remove acidic components such as hydrogen sulfide, carbon dioxide, and mercaptans, oxygen containing compounds, such as carbonyl compounds are also removed. These oxygen containing compounds, particularly acetaldehyde, will undergo polymerization in the presence of the basic wash or scrubbing conditions. In the wash tower, the resulting polymer settles on the trays leading to fouling and thereafter plugging of the trays. Eventually the unit must be shut down for cleaning, which is a costly operation. The basic wash systems, wherein treatment is required to inhibit polymer-based fouling, include amine scrubbers such as monoethanolamine and diethanolamine and caustic (sodium hydroxide) wash systems.

Generally, the basic washing entails contacting the gaseous cracked effluent with an aqueous basic solution in a wash tower to remove hydrogen sulfide, carbon dioxide and mercaptans therefrom. The conditions in the wash tower are conducive for condensation reactions of many enolizable aldehydes (such as acetaldehyde) and/or ketones contained therein.

Several patents relate to methods of inhibiting carbonyl fouling in caustic scrubber.

In U.S. Pat. No. 4,673,489, hydroxylamine and its hydrochloride and hydrogen sulfate salts have been used to inhibit polymer formation caused by condensation reactions of aldehydes contained in caustic scrubber units.

In U.S. Pat. No. 4,952,301, ethylenediamines and water soluble salt forms thereof have been used to inhibit carbonyl based fouling, particularly aldehyde fouling, that often occurs during caustic scrubbing of liquid or gas phase hydrocarbon streams in the base wash unit. U.S. Pat. No. 5,264,114 also discloses the use of amine compounds to inhibit the deposition of foulants during caustic washing.

Carbohydrazide has been disclosed as useful for inhibiting polymeric fouling deposits during the caustic scrubbing of pyrolytically-produced hydrocarbons contaminated with oxygen-containing compounds in U.S. Pat. No. 5,160,425. Hydrazides for the same purpose have been disclosed in U.S. Pat. No. 5,288,394.

In U.S. Pat. No. 5,194,143, an acetoacetate ester is used in a method for inhibiting fouling during caustic washing of hydrocarbons. Amide condensation products of monocarboxylic acids and aliphatic polyamines for the same purpose were disclosed in U.S. Pat. No. 3,364,130. Additionally, U.S. Pat. No. 5,220,104 discloses the use of percarbonate salts for the same purpose.

A method for inhibiting oxygenated hydrocarbon fouling that does not interfere with overall plant operations or in the operation of individual process units would be highly desirable. Such a method would also have the additional advantage of reducing the concentration of oxygenated hydrocarbons and particularly carbonyl compounds in process units and especially, in product streams. Surprisingly, non-enolizable carbonyl carbonyl compounds, though themselves containing carbonyl groups, have utility for the inhibition of oxygenated hydrocarbon fouling.

SUMMARY OF THE INVENTION

The invention is a method of inhibiting the formation of fouling deposits occurring in an alkaline scrubber used to wash acid gases, which deposits are formed during the scrubbing of pyrolytically produced hydrocarbons contaminated with oxygen-containing compounds with a caustic solution having a pH>7 which comprises adding an effective deposit-inhibiting amount of a non-enolizable carbonyl compound to the caustic solution. The invention is also a method of inhibiting the formation of fouling deposits occurring in spent caustic wash/stripper systems used for hydrocarbon manufacturing processes which are in contact with hydrocarbon processing streams contaminated with oxygen-containing compounds, which deposits are formed in hydrocarbon processing streams contaminated with oxygen-containing compounds while in contact with a caustic solution having a pH>7, which comprises adding an effective deposit-inhibiting amount of a non-enolizable carbonyl compound to the caustic solution. Preferred non-enolizable carbonyl compounds are formaldehyde, glyoxal, benzaldehyde, p-anisaldehyde, formic acid, glyoxalic acid and paraformaldehyde.

DESCRIPTION OF THE INVENTION

The term deposits as utilized herein refers to polymeric residues which are due to oxygen-containing contaminants.

Non-enolizable carbonyl compounds may be utilized for the inhibition of the formation of polymeric fouling deposits in caustic towers and benzene strippers.

The invention is a method of inhibiting the formation of fouling deposits occurring in an alkaline scrubber used to remove acid gases, which deposits are formed during the scrubbing of pyrolytically produced hydrocarbons contaminated with oxygen-containing compounds with a caustic solution having pH>7 which comprises adding an effective deposit-inhibiting amount of a non-enolizable carbonyl compound to the caustic solution.

The non-enolizable carbonyl compound may be selected from the group consisting of formaldehyde, glyoxal, benzaldehyde, p-anisaldehyde, formic acid, glyoxalic acid and paraformaldehyde. In this method, the pyrolytically-produced hydrocarbon may be an olefin. The oxygen-containing compound may be a carbonyl compound. Moreover, the carbonyl compound may be acetaldehyde.

The hydrocarbons may be produced by the pyrolytic cracking of hydrocarbon feedstocks. Those feedstocks may be selected from the group consisting of ethane, propane, butane, naphtha and mixtures thereof. The non-enolizable carbonyl compound may be selected from the group consisting of formaldehyde, glyoxal, benzaldehyde, p-anisaldehyde formic acid, glyoxalic acid and paraformaldehyde. For the practice of this invention, the non-enolizable carbonyl compound is added to the alkaline scrubber in an amount representing a molar ratio of non-enolizable carbonyl to carbonyl from about 25:1 to about 3:1. Preferably, the non-enolizable carbonyl compound is added to the alkaline scrubber in an amount representing a molar ratio of non-enolizable carbonyl to carbonyl from about 10:1 to about 3:1. Most preferably, the non-enolizable carbonyl compound is added to the alkaline scrubber in an amount representing a molar ratio of non-enolizable carbonyl to carbonyl from about 5:1 to about 3:1.

The invention is also a method of inhibiting the formation of fouling deposits occurring in spent caustic wash/stripper systems used for hydrocarbon manufacturing processes which are in contact with hydrocarbon processing streams contaminated with oxygen-containing compounds, which deposits are formed in hydrocarbon processing streams contaminated with oxygen-containing compounds while in contact with a caustic solution having a pH>7, which comprises adding an effective deposit-inhibiting amount of a non-enolizable carbonyl compound to the caustic solution.

The oxygen-containing compound may be a carbonyl compound. Moreover, the carbonyl compound may be acetaldehyde.

The non-enolizable carbonyl compound may be added to the spent caustic wash/stripper system in an amount representing a molar ratio of non-enolizable carbonyl to carbonyl from about 25:1 to about 3:1. Preferably, the ratio is from about 10:1 to about 3:1. Most preferably, the ratio is from about 5:1 to about 3:1.

The inhibitors of the present invention can be added to the individual operational units as neat material or in solution form. A dilute solution may be preferred so that accurate metering of the inhibitor to the individual operating units can be achieved. Additionally, it is noted that the inhibitors of the present invention may be used in conjunction with other chemical treatments, such as anti-foams, corrosion inhibitors, anti-oxidants, dispersants metal deactivators and anti-polymerants.

The solvents suitable for use in diluting the inhibitors of the present invention include water, alcohol, hydrocarbon extraction systems, pyrolysis gasoline and generally any other solvents that are compatible with all or part of the medium in each process unit.

The solution should be added to the system in sufficient quantity to assure that the molar amount of inhibitor is effective to prevent fouling. Treatment ranges of from 1 to 10,000 ppm of inhibitor in the medium may be utilized if no convenient method of measuring carbonyl concentration is available. Where the carbonyl concentration is known or estimable, the inhibitor is preferably added in excess of the carbonyl equivalents.

As applied to treat a spent caustic wash/stripper system, the inhibitors may be added directly to the spent caustic wash/stripper system and/or any associated settling tank or stripper column. However, the preferred method of inhibiting fouling in the stripper is to add the inhibitors to the caustic stream before it is introduced into the stripper.

As utilized herein, the term caustic wash/stripper system is meant to encompass a benzene stripper unit.

The following examples are presented to describe preferred embodiments and utilities of the invention and are not meant to limit the invention unless otherwise stated in the claims appended hereto.

EXAMPLE 1

This experimental procedure was utilized for the qualitative analysis of formaldehyde. Potassium hydroxide (1M, 10 mL) was added to each of two tapered centrifuge tubes. Then, to one of the tubes was added formalin, which is 37 wt % formaldehyde in water, (250 mL, 3.1 mmoles formaldehyde). The tube was capped and shaken. Next, acetaldehyde (100 mL, 1.79 mmoles) was added to both tubes and the tubes were capped and shaken. The tubes were allowed to sit undisturbed for 1 week at room temperature.

After one week, a red-orange precipitate had settled from the blank tube (no non-enolizable carbonyl added). The tube dosed with formaldehyde contained no precipitate. The solution was slightly orange, but clear and translucent. Thus, formaldehyde effectively inhibited the formation and precipitation of polymeric foulant from the caustic solution.

EXAMPLE 2

Benzaldehyde and p-anisaldehyde were qualitatively analyzed according to the procedure described in Example 1, with slight modifications. Three tubes were utilized to perform the test: one blank, one treated with 250 mL of benzaldehyde, and one treated with 250 mL of p-anisaldehyde. The aldehydes were not miscible with the caustic solution. The tubes were shaken vigorously to emulsify the mixtures but two phases eventually settled out: a large caustic bottom phase and a small organic upper phase of aldehyde.

Nevertheless, after sitting overnight, the blank tube contained precipitated foulant but the tubes containing benzaldehyde and p-anisaldehyde remained clear and free of precipitate. This experiment shows that the aldehydes do not necessarily need to be miscible with caustic to inhibit polymerization of the acetaldehyde.

EXAMPLE 3

Glyoxal and paraformaldehyde were qualitatively analyzed in the following manner. Potassium hydroxide (1M, 10 mL) was added to each of three tapered centrifuge tubes. Then, paraformaldehyde (400 mg) was added to one of the tubes. To one of the other tubes was added a 40% solution of glyoxal in water (1.1 mL, ~8 mmol). The tubes were capped and shaken. Next, acetaldehyde (100 mL, 1.79 mmoles) was added to each tube and the tubes were capped and shaken vigorously.

After sitting undisturbed overnight at room temperature, 0.5 mL of orange solids had precipitated from the blank tube. The tubes treated with paraformaldehyde and glyoxal were free and clear of precipitate. The solutions were colorless and translucent.

EXAMPLE 4

A determination of the weight equivalents of paraformaldehyde required for inhibition of the caustic-catalyzed polymerization of acetaldehyde was made in the following manner. Paraformaldehyde was added to 10 vials as shown in Table I below. Potassium hydroxide (1M, 10 mL) was added to each of the ten scintillation vials plus a blank vial. The vials were capped and shaken vigorously until all of the paraformaldehyde was dissolved.

Next, acetaldehyde (79 mg) was added to each vial and the vials were capped and shaken. After sitting undisturbed overnight at room temperature, orange solids had precipitated from the blank vial and vials 1 and 3. Vial 2 was clear and contained no solids. Vials 4–10 were clear and free of polymer.

This test was repeated exactly as described except that a maximum of only five weight equivalents of paraformaldehyde was used. The results of this test showed that the blank and vial 1 contained precipitated orange solids. Vial 2 had developed a yellow color but contained no solids. Tubes 3–5 were clear and free of solids or color.

This test was repeated a third time and the appearance of the vials was evaluated after 3–4 hours instead of overnight. In this test, the blank and vial 1 contained precipitated orange solids. Vials 2 and 3 developed a pale yellow color but contained no solids. Tubes 4–5 were clear and free of solids or color.

The overall results show that only two weight equivalents of paraformaldehyde prevent the precipitation of solids formed by the caustic-catalyzed 1 weight equivalent of acetaldehyde.

TABLE I

| vial number | paraformaldehyde (mg) | equivalents per wt of acetaldehyde |
| --- | --- | --- |
| 0 | 0 | 0 |
| 1 | 80 | 1 |
| 2 | 160 | 2 |
| 3 | 240 | 3 |
| 4 | 320 | 4 |
| 5 | 400 | 5 |
| 6 | 480 | 6 |
| 7 | 560 | 7 |
| 8 | 640 | 8 |
| 9 | 720 | 9 |
| 10 | 800 | 10 |

EXAMPLE 5

The determination of the weight equivalents of glyoxal required for inhibition of the caustic-catalyzed polymerization of acetaldehyde was made in the following manner. Portions of a 40% glyoxal in water were added to 10 vials as shown in Table II below.

Potassium hydroxide (1M, 10 mL) was then added to each of the ten scintillation vials plus a blank vial. The vials were capped and shaken vigorously to completely mix the liquids. Next, acetaldehyde (79 mg) was added to each vial and the vials were capped and shaken.

After sitting undisturbed for 3–4 hours at room temperature, orange solids had precipitated from the blank vial and vials 1–6. The liquid in vials 1–6 was also slightly cloudy; the cloudiness decreased with increasing vial number (glyoxal content). Vials 7–10 were clear and free of polymer. The liquid in vial 7 was bright yellow. The color of the liquids in vials 8–10 was pale yellow, probably from the large concentration of glyoxal.

These results show that 14 weight equivalents of glyoxal were required to completely prevent the precipitation of solids formed by the caustic-catalyzed polymerization of 1 weight equivalent of acetaldehyde.

TABLE II

| vial number | glyoxal (mg) | equivalents per wt of acetaldehyde |
| --- | --- | --- |
| 0 | 0 | 0 |
| 1 | 124 | 2 |
| 2 | 248 | 4 |
| 3 | 372 | 6 |
| 4 | 496 | 8 |
| 5 | 620 | 10 |
| 6 | 744 | 12 |
| 7 | 868 | 14 |
| 8 | 992 | 16 |
| 9 | 1116 | 18 |
| 10 | 1240 | 20 |

Changes can be made in the composition, operation and arrangement of the method of the present invention described herein without departing from the concept and scope of the invention as defined in the following claims:

We claim:

1. A method of inhibiting the formation of fouling deposits occurring in an alkaline scrubber used to remove acid gases, which deposits are formed during the scrubbing of pyrolytically produced hydrocarbons contaminated with oxygen-containing compounds with a caustic solution having pH>7 which comprises adding an effective deposit-inhibiting amount of a non-enolizable carbonyl compound to the caustic solution.

2. The method of claim 1, wherein the non-enolizable carbonyl compound is selected from the group consisting of formaldehyde, glyoxal, benzaldehyde, p-anisaldehyde, formic acid, glyoxalic acid and paraformaldehyde.

3. The method of claim 1, wherein the oxygen-containing compounds are carbonyl compounds.

4. The method of claim 3, wherein the carbonyl compound is acetaldehyde.

5. The method of claim 3, wherein the non-enolizable carbonyl compound is added to the alkaline scrubber in an amount representing a molar ratio of non-enolizable carbonyl to carbonyl from about 25:1 to about 3:1.

6. The method of claim 3 wherein the non-enolizable carbonyl compound is added to the alkaline scrubber in an amount representing a molar ratio of non-enolizable carbonyl to carbonyl from about 10:1 to about 3:1.

7. The method of claim 3 wherein the non-enolizable carbonyl compound is added to the alkaline scrubber in an amount representing a molar ratio of non-enolizable carbonyl to carbonyl from about 5:1 to about 3:1.

8. The method of claim 1, wherein the hydrocarbons are produced by the pyrolytic cracking of hydrocarbon feedstocks.

9. The method of claim 8, wherein the hydrocarbon feedstocks are selected from the group consisting of ethane, propane, butane, naphtha and mixtures thereof.

10. A method of inhibiting the formation of fouling deposits occurring in spent caustic wash/stripper systems used for hydrocarbon manufacturing processes which are in contact with hydrocarbon processing streams contaminated with oxygen-containing compounds, which deposits are formed in hydrocarbon processing streams contaminated with oxygen-containing compounds while in contact with a caustic solution having a pH>7, which comprises adding an effective deposit-inhibiting amount of a non-enolizable carbonyl compound to the caustic solution.

11. The method of claim 10, wherein the non-enolizable carbonyl compound is selected from the group consisting of formaldehyde, glyoxal, benzaldehyde, p-ansaldehyde, formic acid, glyoxalic acid and paraformaldehyde.

12. The method of claim 10, wherein the oxygen-containing compounds are carbonyl compounds.

13. The method of claim 12, wherein the carbonyl compound is acetaldehyde.

14. The method of claim 12, wherein the non-enolizable carbonyl compound is added to the spent caustic wash/stripper system in an amount representing a molar ratio of non-enolizable carbonyl to carbonyl from about 25:1 to about 3:1.

15. The method of claim 12 wherein the non-enolizable carbonyl compound is added to the spent caustic wash/stripper system in an amount representing a molar ratio of non-enolizable carbonyl to carbonyl from about 10:1 to about 3:1.

16. The method of claim 12 wherein the non-enolizable carbonyl compound is added to the spent caustic wash/stripper system in an amount representing a molar ratio of non-enolizable carbonyl to carbonyl from about 5:1 to about 3:1.

* * * * *